Figure 1:
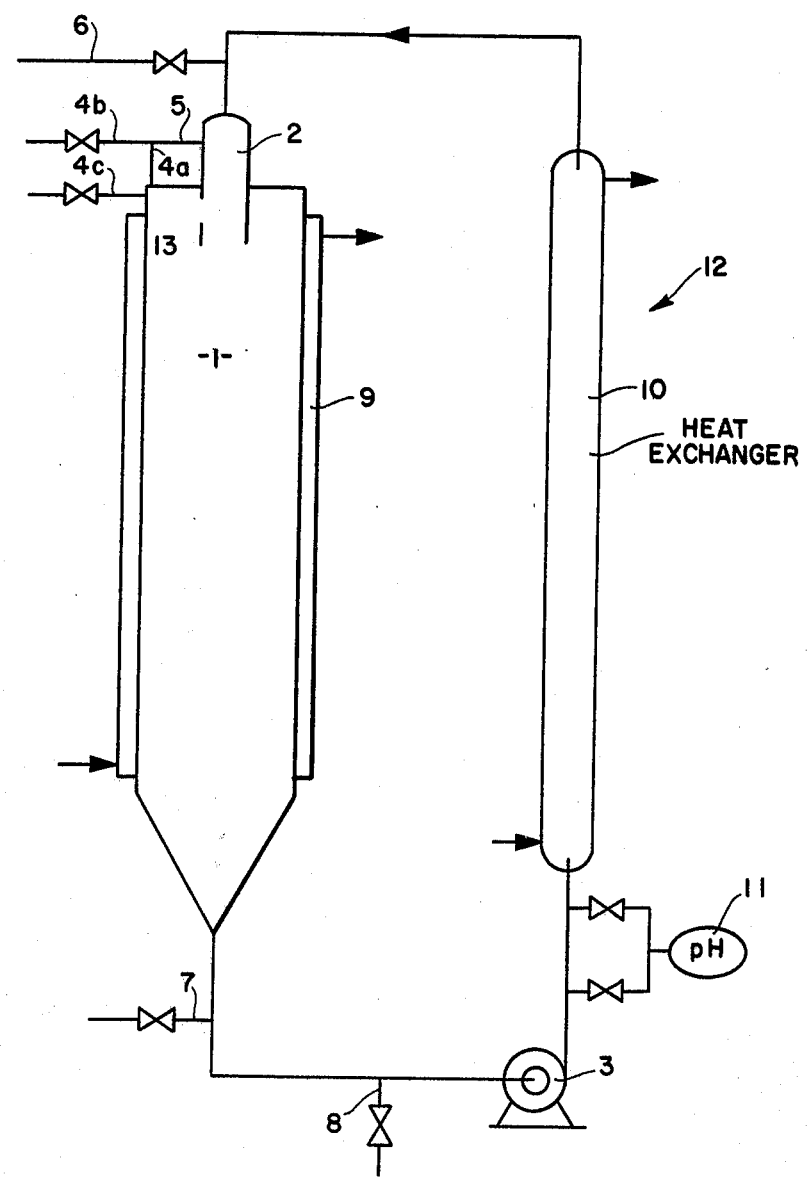

United States Patent [19]

El-Chahawi et al.

[11] 4,424,375

[45] Jan. 3, 1984

[54] METHOD AND APPARATUS FOR PERFORMING CARBONYLATION REACTIONS

[75] Inventors: Moustafa El-Chahawi, Troisdorf; Uwe Prange, Niederkassel-Ranzel; Hermann Richtzenhain, Much-Schwellenbach; Wilhelm Vogt, Cologne, all of Fed. Rep. of Germany

[73] Assignee: Dynamit Nobel AG, Troisdorf-Cologne, Fed. Rep. of Germany

[21] Appl. No.: 274,108

[22] Filed: Jun. 16, 1981

Related U.S. Application Data

[63] Continuation of Ser. No. 154,161, May 28, 1980, abandoned, which is a continuation of Ser. No. 744,357, Nov. 23, 1976, abandoned.

[30] Foreign Application Priority Data

Dec. 1, 1975 [DE] Fed. Rep. of Germany ....... 2553931

[51] Int. Cl.$^3$ ............................................. C07C 69/76
[52] U.S. Cl. ..................................... 560/105; 560/55; 560/76; 560/100; 560/102; 560/187; 560/204; 560/232; 560/233; 562/406
[58] Field of Search ................... 560/105, 55, 76, 100, 560/102, 187, 204, 232, 233; 562/406

[56] References Cited

U.S. PATENT DOCUMENTS 3,816,515 6/1974 Kelham ............................... 560/105
3,974,202 8/1976 El-Chahawi ........................ 560/105

OTHER PUBLICATIONS

Falbe, Carbon Monoxide in Organic Synthesis, pp. 118–120 (1970).
Perry, Chemical Engineer's Handbook, Fourth Ed., pp. 18-63 to 18-68 and 18-77 (1963).

*Primary Examiner*—Paul J. Killos
*Attorney, Agent, or Firm*—Felfe & Lynch

[57] ABSTRACT

Improvement in the process of producing carboxylic acid esters or salts involving contacting a halogen alkyl compound with carbon monoxide and a basic substance in the presence of a carbonylation catalyst for carbonylation of the halogen alkyl and production of the corresponding ester or salt of the basic substance. The improvement involves performing the contacting in a reaction vessel, circulating a liquid mass of the halogen alkyl, basic substance and carbonylation catalyst through the vessel and maintaining a carbon monoxide atmosphere in the vessel, injecting the circulating liquid mass into the vessel with a nozzle to spray the liquid mass into the vessel and intimately mixing the liquid mass with carbon monoxide in the nozzle for injection of carbon monoxide into the vessel with the sprayed liquid mass.

6 Claims, 1 Drawing Figure

METHOD AND APPARATUS FOR PERFORMING CARBONYLATION REACTIONS

This is a continuation of application Ser. No. 154,161 filed May 28, 1980 (abandoned) which is, in turn, a continuation of application Ser. No. 744,357 filed Nov. 22, 1976 (abandoned).

BACKGROUND

The present invention relates to a method and an apparatus for the carbonylation of halogen alkyl compounds. Halogen alkyl compounds can be reacted under appropriate conditions with carbon monoxide and alcohols in the presence of carbonylation catalysts and basic substances to form carboxylic acid esters (German "Auslegeschrift" Nos. 2,240,398 and 2,240,399) and carboxylic acid salts.

In the "Auslegeschriften" referred to above, the reaction is performed in a flask provided with a high-speed stirrer under light carbon monoxide pressure, in order to achieve a good substance exchange between the gas phase and the liquid.

The technical performance of the carbonylation, however, is not satisfactory. It has been found that the speed of the reaction depends on the speed of the stirring, and therefore can hardly be further increased in this manner.

It is necessary that the basic substances necessary for the reaction, such as alkali alcoholates for example, be delivered over a long period of time amounting to several hours, since otherwise there is danger of a substitution reaction between the halogen alkyl compound and the basic substance, thereby reducing the selectivity of the reaction.

These difficulties are encountered to a greater extent in the application of these reactions on a technical scale.

Consequently, the problem existed of increasing the speed of the reaction and nevertheless suppressing the secondary reactions. A method thus had to be found which would make it possible to eliminate the difficulties described while at the same time reacting halogen alkyl compounds and carbon monoxide to produce carboxylic acid esters and carboxylic acid salts in high yields without the use of expensive technical apparatus.

THE INVENTION

It has been found that these above-mentioned difficulties in the production of carboxylic acid esters and carboxylic acid salts can be avoided in the reaction of halogen alkyl compounds with carbon monoxide or gas mixtures containing carbon monoxide, and alkali compounds, in the presence of carbonylation catalysts, if the reaction is performed in an apparatus in which the reaction solution, with a supply of alkali compounds, is sprayed into a carbon monoxide atmosphere and constantly recirculated, while an intense mixing together of the reactants takes place.

The subject matter of the invention, therefore, is a method of preparing carboxylic acid esters and, in some cases, carboxylic acid salts, by the carbonylation of halogen alkyl compounds in the presence of carbon monoxide, an alkaline substance, and carbonylation catalysts, which is characterized by the fact that the reaction mixture is intimately mixed with carbon monoxide through a nozzle by means of a recirculating pump, and is sprayed in very finely divided form into the carbon monoxide atmosphere of the carbonylation reactor.

Additional subject matter of the invention is an apparatus for the performance of carbonylation reactions, characterized by a controlled-temperature reactor, and a recirculating system provided with a pump and running from the reactor to a nozzle which is supplied with carbon monoxide and which finely sprays the reaction material into the gas chamber of the reactor.

Essential components of the apparatus are a recirculating pump and an atomizing nozzle, in the manner, for example, of a Venturi nozzle.

It is surprising that the absorption and reaction of the carbon monoxide is promoted in a nozzle, and that the atomization promotes a good distribution of the carbon monoxide in the liquid phase instead of promoting the separation of the liquid and gaseous phases.

The recirculation pump delivers the stream of liquid to the nozzle, which aspirates carbon monoxide from the reaction chamber and at the same time atomizes the reaction solution into the carbon monoxide atmosphere of the reactor. In the nozzle the reaction solution and the carbon monoxide are intimately mixed together and enter together in finely divided form into the carbon monoxide gas chamber of the reactor. In the lower part of the reactor the reaction solution collects, and is then constantly fed by the recirculating pump to the nozzle.

The carbonylation of halogen alkyls can be performed in the recirculating apparatus of the invention at CO pressures beginning at 0.1 bar.

Pressures of 1 to 10 bars are desirable and preferred, although pressures of up to about 100 bars are possible, and are advantageous for the production of certain esters.

Very generally, the halogen alkyl compounds in question are substances of the formula R—CH$_2$—X, wherein X is one of the halogens, chlorine, bromine or iodine, preferably chlorine. They are, for example, those in which R represents a phenyl moiety or a substituted phenyl moiety with one or more substituents such as chlorine, alkyl, especially methyl, or alkoxy, from which the corresponding aryl acetic acid esters are produced; furthermore, R can represent a naphthyl moiety or other moieties of condensed aromatic nuclei, from which naphthylacetic esters are prepared; or, R represents

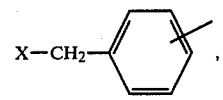

through which the esters of phenylenediacetic acids or obtainable; furthermore, R can represent —COOR', through which malonic esters with the alkyl group R' are accessible, the latter having preferably 1 to 8 carbon atoms; in addition, it can be an alkyl or alkenyl moiety, as well as a substituted alkyl or alkenyl moiety in which the chain length can amount to from 1 to about 24 carbon atoms; examples thereof are the preparation of cyanacetic acid alkyl esters from chloroacetonitrile, beta-alkoxybutyric acid esters from allyl chloride with the simultaneous addition of alcohol from the solvent, and crotonic acid esters, and, likewise, α,β-unsaturated carboxylic acid esters from α,β-unsaturated halides.

It is to be understood that the alcohol moiety of the esters is that which has been selected in the alkyl moiety of the alcoholate that is used, and which can have basically any desired chain length and branching, though in general it will be from 1 to about 24, and preferably up to about 8 carbon atoms.

It is furthermore to be understood that the basic substances available for the preparation of the corresponding carboxylic acid salts are alkali lyes or lime, the preparation of the acids then being effected by liberation with strong mineral acids such as hydrochloric acid.

As carbonylation catalysts the metal carbonyls can be used, i.e., compounds of metal and carbon monoxide, especially $Co_2(CO)_8$, and $Ni(CO)_4$, but also, for example, $Fe(CO)_5$, either in the ready-formed state or produced from a suitable salt and carbon monoxide before or during the reaction. Additions of water-soluble compounds containing sulfur are possible, such as alkali thiosulfate or alkali dithionites, and of metal powders, such as powders of manganese and/or iron, for example.

The alkaline substances serve for the adjustment of the pH, which generally is to be between about 5 and about 10, but frequently the best yield can be achieved within a narrower pH range.

Insofar as the alkali alcoholates, especially of sodium or also potassium, are used as the alkaline substances, they serve simultaneously as reagents for the forming of the alcohol moiety of the ester or additionally for the introduction of an alkoxy group.

Alkali lyes and CaO lead to the formation of the salts of the particular acid involved. Additional alkaline substances, such as amines for example, can be used but are not preferred. The basic substances are preferably dissolved in an alcohol or, if required, suspended therein, generally in the alcohol corresponding to the alcohol moiety of the ester.

To prevent insofar as possible any secondary reactions of the halogen methyl compound with the alkali compound, the pH of the reaction mixture is continually monitored at a pH measuring point.

The apparatus of the invention will be explained with the aid of the drawing showing an embodiment thereof.

FIG. 1 represents an apparatus for the performance of carbonylation reactions in a controlled-temperature reactor, and a system connected thereto for the recirculation of the reaction material which is fed into the reactor through a nozzle together with carbon monoxide.

The reactor 1 is of such dimensions that at least 10 to 20% of its capacity is available as a gas chamber, and it can be temperature-controlled through a jacket 9, i.e., it can be heated or cooled as required. The recirculating system 12 with pump 3 leads to a nozzle 2 mounted in the upper portion of the reactor 1 and extending into the carbon monoxide gas chamber of said reactor 1. The feeding of carbon monoxide to nozzle 2 is accomplished through the lateral aspiration connection 5 to which fresh carbon monoxide can be fed selectively through line 4b, or to which carbon monoxide from the gas chamber of the reactor can be delivered through supply line 4a.

Carbon monoxide can be introduced directly into the gas chamber of the reactor through supply line 4c, and the opening 13 which can be present if desired in the wall of the nozzle permits the additional entry of carbon monoxide from the gas chamber of the reactor into the nozzle. The feed points 6 and 7 serve for the feeding of starting substances and of the alkaline substance, the feeding of the alkaline substance at 6 being preferred.

The removal of the product is accomplished through the drain valve 9. The controlled-temperature heat exchanger 9 can, if required, supplement the heat exchanger 10.

The pH is measured in the pH meter located in the by-pass at 11.

With this apparatus, brief reaction times and a high selectivity of the reaction are achieved. In addition, the construction of the apparatus in accordance with the invention assures a rapid removal of reaction heat.

The operation of the apparatus can, in general, take place in the following manner.

An alcoholic solution of metal carbonyl and halogen alkyl compound are fed into the apparatus through feed point 7 under a nitrogen atmosphere. Through line 4a a carbon monoxide pressure of, for example, 4 to 6 bars, is established. The reaction mixture is fed to the circuit by means of the recirculating pump 3 and at the same time brought to the reaction temperature of 55° C. through the heat exchanger 9. Then alkali compound is proportioned through the feeder 6 such that the desired pH remains constant.

At the end of the feeding period, the mixture is given a post-reaction period of 15 to 60 minutes depending on the type of reaction, and then it is cooled by means of the heat exchanger 9. Then the pressure is relieved and the reactor is rinsed out with nitrogen, and the reaction mixture is removed from the apparatus through the drain valve 8. After the separation of alkali halide, the solvent is removed by distillation and then the carboxylic acid ester is isolated.

EXAMPLES

The following examples attest to the high yields and purities of the substances, as well as the advantageously short reaction times, although they refer to only a few, typical products out of the many that can be produced by carbonylation reaction.

EXAMPLE A

Using 30 g of $Co_2(CO)_8$ in 2 liters of methanol, 3 kg of benzyl chloride and 4550 g of 30% sodium methylate, the following results were obtained with various feeding periods followed by one hour of post-reaction time:

| Feed time in hours | Distillate in grams | Product Distribution in % | |
|---|---|---|---|
| | | $C_6H_5CH_2OCH_3$ | $C_6H_5CH_2COOCH_3$ |
| 1 | 3275 | 1.5 | 96.5 |
| 2 | 3395 | 1.0 | 97.0 |
| 3 | 3353 | 0.9 | 97.5 |
| 4 | 3367 | 1.0 | 97.5 |

EXAMPLE B

Using 125 g of $Co_2(CO)_8$ in one liter of ethanol, 3.06 kg of chloroacetic acid ethyl ester and 7.03 kg of 21.9% sodium ethylate, the following amounts were obtained, at a pH of 7.0, a feeding period of 5½ hours, and a transformation of 90%:
290 g of chloroacetic acid ethyl ester
30 g of acetic acid ethyl ester (yield 1.3%)
3430 g of malonic acid diethyl ester (yield 95%)

EXAMPLE C

Using 90 g of $Ni(CO)_4$, 1 liter of methanol, 3.06 kg of allyl chloride and 7.3 kg of 30% sodium methylate containing 0.9 wt.-% of NaOH, the following results were obtained at a pH of 9.9 after one hour of feeding time and one hour of post-reaction:
160 g of beta-methoxybutyric acid methyl ester (yield 3%), and
3.61 kg of crotonic acid methyl ester (yield 95%).

What is claimed is:

1. In the process for producing carboxylic acid esters or salts by contacting a halogen alkyl compound of the formula $R-CH_2$-halogen with carbon monoxide and a basic substance for maintaining a pH in the reaction mixture, in the range of 5 to 10, in the presence of a metal carbonyl carbonylation catalyst for carbonylation of the halogen alkyl and production of the corresponding ester or salt of the basic substance, the improvement which comprises performing said contacting in a reaction vessel, circulating a liquid mass of the halogen alkyl, basic substance and metal carbonyl carbonylation catalyst through the vessel and maintaing a carbon monoxide atmosphere in the vessel with a pressure of 0.1 to 100 bar, injecting the circulating liquid mass into the vessel with a nozzle to spray the liquid mass into the vessel and intimately mixing the liquid mass with carbon monoxide in the nozzle for injection of carbon monoxide into the vessel with the sprayed liquid mass.

2. Process of claim 1, wherein the basic substance is an alkali alcoholate, alkali, lye, or lime.

3. Process of claim 1, wherein the basic substance is an alkali alcoholate, and an alcohol is included in said liquid mass.

4. Process of claim 1 wherein the metal carbonyl carbonylation catalyst is a cobalt, iron or nickel carbonyl compound.

5. The process of claim 2 wherein the metal carbonyl carbonylation catalyst is a cobalt, iron or nickel carbonyl compound.

6. The process of claim 3 wherein the metal carbonyl carbonylation catalyst is a cobalt, iron or nickel carbonyl compound.

* * * * *

UNITED STATES PATENT AND TRADEMARK OFFICE
CERTIFICATE OF CORRECTION

PATENT NO. : 4,424,375
DATED : January 3, 1984
INVENTOR(S) : El-Chahawi et al

It is certified that error appears in the above-identified patent and that said Letters Patent is hereby corrected as shown below:

In claim 1, column 5, line 10, after "R-CH$_2$- halogen" insert --, wherein

R represents a phenyl moiety or a substituted phenyl moiety with one or more substituents selected from chlorine, alkyl, or alkoxy; a naphthyl moiety, or other moieties of condensed aromatic nuclei; X-CH$_2$-⌬ ; -COOR' where R' is alkyl of 1 to 8 carbon atoms; alkyl or alkenyl, or substituted alkyl or alkenyl moiety with a chain length of 1 to about 24 carbon atoms, and X is halogen.

Signed and Sealed this

Seventeenth Day of September 1985

[SEAL]

Attest:

Attesting Officer

DONALD J. QUIGG

Commissioner of Patents and
Trademarks—Designate